United States Patent
Perner et al.

(10) Patent No.: US 12,128,119 B2
(45) Date of Patent: Oct. 29, 2024

(54) ESSENTIALLY ANHYDROUS HAIR-TREATMENT COMPOSITIONS COMPRISING A POLYURETHANE LATEX POLYMER AND BIS-UREA DERIVATIVE

(71) Applicant: L'OREAL, Paris (FR)

(72) Inventors: Allison Perner, Metuchen, NJ (US); Anand Mahadeshwar, Scotch Plains, NJ (US); Miao Wang, Westfield, NJ (US); Marie Huynh, Monmouth Junction, NJ (US); Bayle Augustin, Union, NJ (US); Lindsay Menzer, Randolph, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/581,993

(22) Filed: Apr. 28, 2017

(65) Prior Publication Data

US 2018/0311131 A1    Nov. 1, 2018

(51) Int. Cl.
| | |
|---|---|
| *A61K 8/31* | (2006.01) |
| *A61K 8/37* | (2006.01) |
| *A61K 8/45* | (2006.01) |
| *A61K 8/58* | (2006.01) |
| *A61K 8/87* | (2006.01) |
| *A61K 8/891* | (2006.01) |
| *A61Q 5/02* | (2006.01) |
| *A61Q 5/12* | (2006.01) |

(52) U.S. Cl.
CPC ............... *A61K 8/31* (2013.01); *A61K 8/37* (2013.01); *A61K 8/45* (2013.01); *A61K 8/585* (2013.01); *A61K 8/87* (2013.01); *A61K 8/891* (2013.01); *A61Q 5/12* (2013.01); *A61K 2800/31* (2013.01); *A61Q 5/02* (2013.01)

(58) Field of Classification Search
CPC ... A61K 8/42; A61K 8/04; A61K 8/25; A61K 8/31; A61K 8/37; A61K 8/87; A61K 8/89; A61K 2800/31; A61K 2800/882; A61K 2800/884; A61Q 5/02; A61Q 5/12
See application file for complete search history.

(56) References Cited

U.S. PATENT DOCUMENTS

| | | | |
|---|---|---|---|
| 6,358,502 B1 | 3/2002 | Tanabe et al. | |
| 7,226,580 B2 | 6/2007 | Amalric et al. | |
| 2004/0198895 A1* | 10/2004 | Ascione | A61K 8/8152 524/523 |
| 2009/0060858 A1 | 3/2009 | Schwarzwaelder et al. | |
| 2011/0144208 A1* | 6/2011 | Feltin | A61K 8/31 514/597 |
| 2013/0224139 A1* | 8/2013 | Hong | A61K 8/42 424/65 |
| 2014/0342968 A1 | 11/2014 | Hourigan et al. | |
| 2015/0004114 A1* | 1/2015 | Tan | A61Q 5/06 424/70.13 |
| 2015/0004117 A1 | 1/2015 | Tan et al. | |
| 2015/0004119 A1 | 1/2015 | Tan et al. | |
| 2015/0004121 A1* | 1/2015 | Tan | A61K 8/87 424/70.16 |
| 2016/0175238 A1 | 6/2016 | Shin et al. | |

FOREIGN PATENT DOCUMENTS

| | | |
|---|---|---|
| DE | 102009054516 A1 | 6/2011 |
| DE | 102010063923 A1 | 6/2012 |

OTHER PUBLICATIONS

Sephora—Perfect Hair Day In-Shower Styler—Living Proof, Retrieved online Apr. 28, 2017.

* cited by examiner

*Primary Examiner* — Doan T Phan
(74) *Attorney, Agent, or Firm* — POLSINELLI PC

(57) ABSTRACT

The instant disclosure relates to essentially anhydrous hair-treatment compositions. The anhydrous hair-treatment compositions typically include: one or more polyurethane latex polymers; one or more bis-urea derivatives; and one or more solvents. Additional components such as silicones, auxiliary agents, etc., can also be included. The instant disclosure also relates to kits that include the essentially anhydrous hair-treatment compositions and to methods for treating hair with the essentially anhydrous hair-treatment compositions.

2 Claims, No Drawings

ESSENTIALLY ANHYDROUS HAIR-TREATMENT COMPOSITIONS COMPRISING A POLYURETHANE LATEX POLYMER AND BIS-UREA DERIVATIVE

FIELD OF THE DISCLOSURE

The instant disclosure relates to essentially anhydrous hair-treatment compositions, which are particularly useful for improving hair manageability, imparting long-lasting style and frizz control to hair, and for protecting hair from damage. Also disclosed are kits that include the essentially anhydrous hair-treatment compositions and methods for using the hair-treatment compositions.

BACKGROUND

For decades, consumers have used hair styling products to help achieve a desired look, including fuller/thicker hair, sleek and straight hair, and frizz-free defined curls. Many different types of hair styling products are commercially available. Nonetheless, consumers desire new multi-functional hair products that are long lasting, convenient, and impart certain cosmetic characteristics to the hair.

Traditional anhydrous oil treatments have been used to nourish and moisturize dull, dry, and damaged hair. These oil treatments also help control frizz and define hair while maintaining a natural look, but the performance of oil treatments is limited, especially in terms of long lasting shape control. In particular, traditional oil treatments do not typically provide benefits such as shaping memory, improved volume, strengthening, heat protection, etc. Oil treatments moisturize and control frizz while maintaining a natural look, but lack many additional styling benefits that consumers seek.

Styling products that provide styling benefits such as shaping memory, hold, improved volume, etc. are advertised but these products also suffer from certain drawbacks. For example, many styling products provide protection against external factors such as protection from moisture to minimize or reduce frizziness. To protect against moisture, a water-resistant film or coating can be applied to the hair. Many of these films or coatings are formed with film-forming polymers. Depending on the chemical make-up of the film-forming polymers, they may be either soluble in water, or they may be water insoluble polymers that are solubilized in water via various chemical modifications, such as neutralization. Solutions comprising these polymers tend to be viscous, i.e. as the concentration of the polymer increases its viscosity builds up rapidly. Translated to styling applications, as the solvent evaporates, the polymer solution becomes thicker on the hair surface, leaving a sticky or tacky film residue on the hair. This often leaves hair with a stiff and/or "crunchy" feeling (i.e. the films become hard and brittle and therefore have a crunchy feel or sound when manipulated), which is undesirable to many consumers.

Consumers desire new multi-functional hair products that have a natural look and feel, impart good styling benefits to hair, are durable, and lack the drawbacks of other products.

SUMMARY OF THE DISCLOSURE

The instant disclosure relates to hair-treatment compositions that include a unique combination of components that function to impart desirable cosmetic properties to the hair. For example, the hair-treatment compositions are useful for improving hair manageability, imparting long-lasting style and frizz control to hair, and for protecting hair from damage, especially heat damage. Also, consumers find the natural look and feel of hair treated with the compositions to be very appealing. The hair-treatment compositions typically include:

one or more polyurethane latex polymers;
one or more bis-urea derivatives of the following formula:

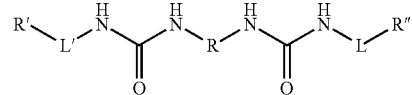

wherein R is a $C_3$-$C_{18}$ linear, branched, or cyclic moiety; and

R' and R" may be the same or different and are selected from the group consisting of $C_1$-$C_{36}$ linear or branched alkanes or aryl alkanes, α-methyl branched $C_2$-$C_{36}$ alkanes, α-methyl branched $C_2$-$C_{36}$ ethers, β-methyl branched $C_2$-$C_{36}$ alkanes, and β-methyl branched $C_2$-$C_{36}$ ethers;

wherein if R' and R" are the same, then both of said groups is selected from the group consisting of α-methyl branched $C_2$-$C_{18}$ ethers and β-methyl branched $C_2$-$C_{18}$ ethers;

wherein L and L' may be same or different and are selected from the group consisting of ethylene oxide chains, propylene oxide chains, and mixtures thereof, and the chains may comprise one or a plurality of repeat units; and one or more solvents.

Additional components such as silicones, auxiliary agents, etc., can also be included. While not wishing to be bound by any particular theory, the inventors believe that the compositions provide the hair with a hydrophobic, flexible, film or film-like coating that is long-lasting, has a very natural look and feel, and improves the styling properties of the hair. The hydrophobic film or film-like coating also provides protection to the hair from damage, for example, damage caused by heat, environmental stress, etc. Furthermore, the film or film-like coating is long lasting, as it can survive repeated washings. Thus, hair maintains the desireable cosmetic properties imparted by the hair-treatment compositions despite subsequent shampooing, rinsing, etc.

The hair-treatment compositions can be used at home during an individual's regular shampooing and/or conditioning routine and therefore do not require special procedures that are only available at professional salons. Accordingly, the instant disclosure also relates to kits that include a hair-treatment composition of the instant disclosure. The kits typically include at least one hair-treatment composition according to the instant disclosure (a hair-treatment composition comprising one or more polyurethane latex polymers, one or more bis-urea derivatives, and one or more solvents) and one or more additional hair-treatment compositions, for example, a shampoo, a conditioner, etc. The various hair-treatment compositions are separately contained in the kits. In some instances, the kits include one or more hair-treatment compositions (according the instant disclosure), a shampoo, and/or a conditioner, all of which are separately contained.

Finally, as mentioned previously, the hair-treatment compositions are unique in their ability to provide hair with improved manageability, long-lasting style and frizz control, and protection. Accordingly, the instant disclosure relates to methods for treating hair, for example, for improving the manageability of hair, for imparting lasting style and frizz control, and for protecting the hair from damage, including damage from heat. More specifically, the hair-treatment compositions may be used in methods for conditioning the hair, providing curl definition to the hair, providing frizz control to the hair, improving ease of combability and detangling, protecting the hair from heat damage, and increasing the appearance of hair volume.

The methods of treating hair according to the disclosure include methods according to various routines. For instance, the hair-treatment composition may be mixed with a shampoo (or conditioner) prior to application to the hair. Alternatively, the hair-treatment composition may be layered on top of (or lathered into) hair to which the shampoo (or conditioner) is already applied. Furthermore, the hair-treatment composition may be applied separate from the shampoo (or conditioner), i.e., applied to the hair after the shampoo (or conditioner) has been rinsed from the hair.

DETAILED DESCRIPTION OF THE DISCLOSURE

The instant disclosure relates to hair-treatment compositions. The term "treatment" in the context of a "hair-treatment" composition encompasses many types of compositions for application to the hair, for example, shampoos, conditioners, hair-rinses, hair lotions, hair gels, mouse-type products, sprays, etc. A hair-treatment composition is characterized by its ability to provide a cosmetic benefit to the hair. As is well-known, a shampoo provides cleansing benefits the hair, a conditioner provides conditioning benefits to the hair, and a gel can provide styling benefits to the hair. Non-limiting examples of additional benefits that can be imparted to hair include frizz control, smoothness, ease of combability, fullness and body, shine, strengthening, damage repair or resistance to damage, including resistance to heat damage, enhancing luster or color, etc.

The hair-treatment compositions of the instant disclosure typically include:
one or more polyurethane latex polymers;
one or more bis-urea derivatives of the following formula:

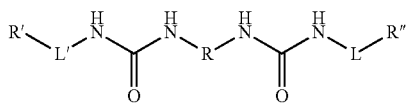

wherein R is a $C_3$-$C_{18}$ linear, branched, or cyclic moiety; and

R' and R" may be the same or different and are selected from the group consisting of $C_1$-$C_{36}$ linear or branched alkanes or aryl alkanes, α-methyl branched $C_2$-$C_{36}$ alkanes, α-methyl branched $C_2$-$C_{36}$ ethers, β-methyl branched $C_2$-$C_{36}$ alkanes, and β-methyl branched $C_2$-$C_{36}$ ethers;

wherein if R' and R" are the same, then both of said groups is selected from the group consisting of α-methyl branched $C_2$-$C_{18}$ ethers and β-methyl branched $C_2$-$C_{18}$ ethers;

wherein L and L' may be same or different and are selected from the group consisting of ethylene oxide chains, propylene oxide chains, and mixtures thereof, and the chains may comprise one or a plurality of repeat units; and one or more solvents.

The one or more polyurethane latex polymers may be in the form of an aqueous polyurethane dispersion, e.g., dispersed as particles in an aqueous dispersion medium. Typically, the polyurethane latex polymers are film forming. Non-limiting examples of polyurethane latex polymers include polyurethane-32, polyurethane-34, polyurethane-35, polyurethane-48, and a mixture thereof. In some cases, polyurethane-34 is particularly well-suited for use in the hair-treatment compositions. A more exhaustive list of polyurethane latex polymers that may be included in the hair-treatment compositions is provided later, under the heading "Polyurethane Latex Polymers."

The total amount of the one or more polyurethane latex polymers may vary but is typically about 0.01 to about 10 wt. %, based on the total weight of the hair-treatment composition. The total amount of the one or more polyurethane latex polymers may be about 0.01 to about 8 wt. %, about 0.01 to about 6 wt. %, about 0.01 to about 5 wt. %, about 0.1 to about 10 wt. %, about 0.1 to about 8 wt. %, about 0.1 to about 6 wt. %, about 0.1 to about 5 wt. %, or about 0.2 to about 4 wt. %.

The hair-treatment compositions include one or more bis-urea derivatives, such as those set forth above. In some instances, the one or more bis-urea derivatives may be selected from the group consisting of compounds of the following formula:

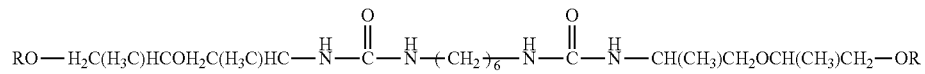

wherein R is a $C_1$-$C_{36}$ linear or branched alkane, a $C_6$-$C_{24}$ linear or branched alkane, or a $C_{10}$-$C_{16}$ linear or branched alkane. A non-limiting example of a bis-urea derivative is as follows:

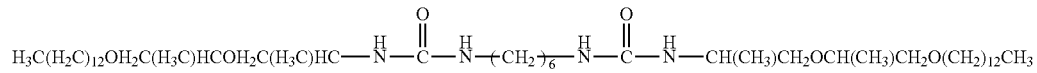

Bis-urea derivatives (such as those described above) and methods for manufacturing the bis-urea derivatives are described in U.S. Pat. No. 8,668,918, which is incorporated herein by reference in its entirety. INCI: Bis-(C12-14 alkyl PPG-4) Hexamethylenediurea is commercially available as Millithix® MT-800 (Milliken).

The total amount of the one or more bis-urea derivatives can vary but is typically about 0.1 to about 35 wt. %, based on the total weight of the hair-treatment composition. In some cases, the total amount of the one or more bis-urea derivatives is about 0.1 to about 30 wt. %, about 0.1 to about 25 wt. %, about 0.1 to about 20 wt. %, about 0.1 to about 15 wt. %, about 1 to about 35 wt. %, about to about 30 wt. %, about 1 to about 25 wt. %, about 1 to about 20 wt. %, or about 1 to about 15 wt. %.

The solvents suitable for use in the essentially anhydrous hair-treatment compositions are typically hydrophobic and/or non-polar. Non-limiting examples include oils, mineral oils, base oils, synthetic hydrocarbons, solid hydrocarbons, semi-solid hydrocarbons, waxes, petroleum distillates, petrolatums, and a mixture thereof. In some cases, the one or more solvents are oils, mineral oil, waxes, alkanes, fatty alcohols, fatty acids, fatty alcohol derivatives, fatty acid derivatives (such as alkoxylated fatty acids or polyethylene glycol esters of fatty acids or propylene glycol esters of fatty acids or butylene glycol esters of fatty acids or esters of neopentyl glycol and fatty acids or polyglycerol/glycerol esters of fatty acids or glycol diesters or diesters of ethylene glycol and fatty acids or esters of fatty acids and fatty alcohols, esters of short chain alcohols and fatty acids), esters of fatty alcohols, hydroxy-substituted fatty acids, waxes, triglyceride compounds, lanolin, ceramide, and a mixture thereof. For instance, one or more fatty compounds may be selected from the group consisting of glycol distearate, PEG-55 propylene glycol oleate, cetearyl alcohol, soybean oil, cetyl esters, isopropyl myristate, cetearyl alcohol, orbigynya oleifera seed oil, propylene glycol dicaprylate/dicaprate, mineral oil, undecane, tridecane, 2-oleamido-1,3-octadecanediol (ceramide), and a mixture thereof. Additionally, in some cases, the one or more fatty compounds may be selected from the group consisting of brassica alcohol, cetyl esters, octyldodecanol, cetearyl alcohol, sunflower seed oil, isostearyl alcohol, and a mixture thereof.

A more exhaustive list of fatty compounds that may be included in the hair-treatment compositions is provided later, under the heading "Solvents."

The total amount of the one or more solvents can vary but is typically about 50 to about 98 wt. %, based on the total weight of the hair-treatment compositions. The total amount of the one or more solvents may be about 55 to about 98 wt. %, about 60 to about 98 wt. %, about 65 to about 98 wt. %, about 70 to about 98 wt. %, about 75 to about 98 wt. %, about 50 to about 97 wt. %, about 55 to about 97 wt. %, about 60 to about 97 wt. %, about 65 to about 97 wt. %, about 70 to about 97 wt. %, about 75 to about 95 wt. %, about 65 to about 80 wt. % or about 85 to about 98 wt. %.

One or more silicones may be included in the hair-treatment compositions. Non-limiting examples of silicones include polyorganosiloxanes, polyalkylsiloxanes, polyarylsiloxanes, polyalkarylsiloxanes, polyestersiloxanes, and a mixture thereof. In particular, suitable examples of silicones include dimethicone, cyclomethicone, amodimethicone, trimethyl silyl amodimethicone, phenyl trimethicone, trimethyl siloxy silicate, and mixtures thereof. For example, in some cases, the hair-treatment compositions may include dimethicone, lauryl PEG/PPG-18/18 methicone, dimethiconol, amodimethicone, cyclomethicone, and a mixture thereof. A more exhaustive list of silicones that may be included in the hair-treatment compositions is provided later, under the heading "Silicones."

The total amount of the one or more silicones may vary but is typically about 0.01 to about 60 wt. %, based on the total weight of the hair-treatment composition. In some cases, the total amount of the one or more silicones is about 0.01 to about 50 wt. %, about 0.01 to about 40 wt. %, about 0.01 to about 30 wt. %, about 0.1 to about 60 wt. %, about 0.1 to about 50 wt. %, about 0.1 to about 40 wt. %, about 0.1 to about 30 wt. %, about 0.5 to about 50 wt. %, about 0.5 to about 40 wt. %, about 0.5 to about 30 wt. %.

One or more auxiliary agents may be included in the hair-treatment compositions. Non-limiting examples of auxiliary agents include silica, silica silicate, fumed silica, amorphous silica, clays, ceramic beads, calcium carbonate, titanium oxides, magnesium oxides, aluminium silicates and derivatives thereof, mixed silicates of natural or synthetic origin, which are optionally hydrated, natural hydrated aluminium silicates, bentonite, kaolin, Nylon, microspheres based on a copolymer of vinylidene chloride/acrylonitrile/methacrylonitrile containing isobutane, micronized or non-micronized vegetable powders, rice grain husk powders, and a mixture thereof.

The total amount of the one or more auxiliary agents may vary but is typically about 0.01 to about 10 wt. %, based on the total weight of the hair-treatment composition. The total amount of the one or more auxiliary agents may be about 0.01 to about 5 wt. %, about 0.01 to about 3 wt. %, about 0.01 to about 2 wt. %, about 0.1 to about 10 wt. %, about 0.1 to about 5 wt. %, about 0.1 to about 3 wt. %, or about 0.1 to about 2 wt. %.

In one embodiment, the hair-treatment compositions of the instant case relate to an essentially anhydrous hair-treatment composition comprising:
  about 0.01 to about 10 wt. %, about 0.01 to about 5 wt. %, or about 0.1 to about 5 wt. % of polyurethane-34;
  about 0.01 to about 15 wt. %, about 0.01 to about 10 wt. %, or about 0.1 to about 10 wt. % of about of BIS-(C12-14 alkyl PPG-4) hexamethylenediurea; and
  about 70 to about 98 wt. % of one or more solvents selected from the group consisting of oils, alkanes, fatty alcohols, fatty acids, fatty alcohol derivatives, fatty acid derivatives, esters of fatty alcohols, esters of fatty acids, hydroxy-substituted fatty acids, oils, and a mixture thereof.

Furthermore, in one embodiment, the hair-treatment compositions of the instant case relate to an essentially anhydrous hair-treatment composition comprising:
  about 0.01 to about 10 wt. %, about 0.01 to about 5 wt. %, or about 0.1 to about 5 wt. % of polyurethane-34;
  about 0.01 to about 15 wt. %, about 0.01 to about 10 wt. %, or about 0.1 to about 10 wt. % of about of BIS-(C12-14 alkyl PPG-4) hexamethylenediurea;
  about 60 to about 98 wt. %, about 65 to about 98 wt. %, or about 70 to about 98 wt. % of one or more solvents selected from the group consisting of oils, alkanes, fatty alcohols, fatty acids, fatty alcohol derivatives, fatty acid derivatives, esters of fatty alcohols, esters of fatty acids, hydroxy-substituted fatty acids, oils, and a mixture thereof;
  about 0.01 to about 40 wt. %, about 0.1 to about 40 wt. %, or about 0.1 to about 30 wt. % of one or more silicones selected from the group consisting of polyorganosiloxanes, polyalkylsiloxanes, polyarylsiloxanes, polyalkarylsiloxanes, polyestersiloxanes, alkylmethylsilicone polyether copolymers, and a mixture thereof, in particular, cyclohexasiloxane and/or polypropylsilsequioxane.

The hair-treatment compositions of the instant disclosure may be incorporated into a kit. For example, the kits may include at least one hair-treatment composition according to the instant disclosure (a hair-treatment composition comprising one or more polyurethane latex polymers, one or more bis-urea derivatives, and one or more solvents) and one or more additional hair-treatment compositions, for example, a shampoo, a conditioner, etc. The various hair-treatment compositions are separately contained in the kits. In some instances, the kits include one or more hair-treatment compositions (according the instant disclosure), a shampoo, and/or a conditioner, all of which are separately contained. The kits may also include one or more hair-treatment compositions (according the instant disclosure), a shampoo, and a conditioner. Instructions, mixing components, brushes, gloves, measuring tools, etc., may also optionally be included in the kits.

The hair-treatment compositions may be packaged in a variety of different containers, such as, for example, a ready-to-use container. Non-limiting examples of useful packaging include tubes, jars, caps, unit dose packages, and bottles, including squeezable tubes and bottles. The packaging may be configured so that it can be attached to a wall, such as a wall in a bathroom, including walls of a shower or tub. For example, the packaging can be a container that is configured to attach to a wall, such that when pressure is applied to the container, the composition contained therein is expelled from one or more openings in the container. In some cases, the packaging is a tube, such as a tube with two compartments, or dual tubes, each forming a separate compartment. Each compartment may include a different composition. For example, one tube or compartment may include a hair-treatment composition according to the instant disclosure, and the other tube may include a composition to be used with the hair-treatment composition, for example, a shampoo, a conditioner, an all-in-one shampoo/conditioner (i.e., a conditioning shampoo; also referred to as a "co-wash"). Both the hair-treatment composition and the additional composition can expelled together (at the same time) or individually. If expelled together, the two compositions can be mixed in the hands and the mixture applied to the hair.

Methods of treating hair according to the disclosure may vary but typically include applying a hair-treatment composition of the instant disclosure to the hair (wet, damp, or dry hair), allowing the hair-treatment to remain on the hair for a sufficient amount of time, and rinsing the hair-treatment compositions from the hair. The hair-treatment composition may be applied to the hair in a sequence with other hair-treatment compositions. For example, the hair-treatment compositions may be applied to the hair before shampooing the hair, after shampooing the hair, before conditioning the hair, and/or after conditioning the hair. The hair-treatment compositions, however, are not required to be used in a sequence.

In some case, the hair-treatment compositions are used in conjunction with additional hair-treatment compositions in a routine, for example, during an individual's normal showering/bathing routine. The hair-treatment composition may be applied to the hair individually or may be combined with one or more additional hair-treatment compositions. Combining the hair-treatment compositions with one or more additional hair treatment compositions (e.g., a shampoo, a conditioner, a rinse, etc.) can be useful for eliminating multiple steps from a routine. For instance, the hair-treatment composition may be mixed with a shampoo (or conditioner) prior to application to the hair. In this case, the mixture of the shampoo (or conditioner) and the hair-treatment composition are simultaneously applied to the hair during the cleansing or conditioning process and simultaneously rinsed from the hair. Alternatively, the hair-treatment composition may be layered on top of (or lathered into) hair to which a shampoo (or conditioner) has already been applied or vice versa. In this case, the hair-treatment composition may be applied to the hair and without rinsing it from the hair, a shampoo (or conditioner) is then subsequently applied to the hair. Alternatively, the shampoo (or conditioner) may be first applied to the hair and without rinsing the shampoo (or conditioner) from the hair, the hair-treatment composition is also applied to the hair.

When used in conjunction with a shampoo and/or a conditioner, the hair-treatment composition may be mixed or used with the shampoo and/or conditioner in a ratio of about 1:10 to about 10:1, about 1:5 to about 5:1, about 1:3 to about 3:1, about 1:2 to about 2:1, about 1:1 to about 4:1, about 1:1 to about 3:1, or about 1:1 to about 2:1 (hair-treatment composition of the instant disclosure:shampoo/conditioner, etc.).

The hair-treatment compositions may be allowed to remain on the hair for a minimum amount of time before being rinsed from the hair, but allowing the hair-treatment composition to remain on the hair for an extended period of time is not needed. Conveniently, the hair-treatment compositions can be applied and allowed to remain on the hair for a period of time that is typical for regular shampooing and/or conditioning. For example, the hair-treatment composition (whether combined with another hair-treatment composition such as a shampoo or conditioner) may be applied to the hair and allowed to remain on the hair for a few seconds (1, 2, 3, or 5 seconds) up to about 1, about 2, about 5, about 10, about 15, about 20, about 25 or about 30 minutes.

When the hair-treatment composition is not being mixed with another hair treatment composition prior to application to the hair, the hair-treatment composition may be applied to the hair immediately after or before the hair it treated with another hair treatment composition (e.g., a shampoo and/or a conditioner). For example, the hair-treatment compositions may be applied to the hair within about 1, 2, 5, 10, or 20 minutes before or after a shampoo and/or a conditioner is applied to the hair.

Finally, as mentioned previously, the hair-treatment compositions are unique in their ability to provide hair with improved manageability, long-lasting style and frizz control, and protection. Accordingly, the instant disclosure relates to methods for treating hair, for example, for improving the manageability of hair, for imparting lasting style and frizz control, and for protecting the hair from damage. More specifically, the hair-treatment compositions may be used in methods for conditioning the hair, providing curl definition to the hair, providing frizz control to the hair, improving ease of combability and detangling, protecting the hair from damage, and increasing the appearance of hair volume.

More exhaustive but non-limiting lists of components useful in the hair-treatment compositions disclosed herein are provided below.

Polyurethane Latex Polymers

Polyurethane latex polymers that be used in the instant hair-treatment compositions include, polyurethane latex polymers such as aqueous polyurethane dispersions comprising the reaction products of (i), (ii), and/or (iii), defined below.

Reaction product (i) may be any prepolymer according to the formula:

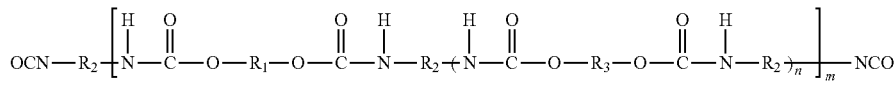

wherein R1 is chosen from bivalent radicals of a dihydroxyl functional compound, R2 is chosen from hydrocarbon radicals of an aliphatic or cycloaliphatic polyisocyanate, and R3 is chosen from radicals of a low molecular weight diol, optionally substituted with ionic groups, n ranges from about 0 to about 5, and m is greater than about 1.

Suitable dihydroxyl compounds for providing the bivalent radical R1 include those having at least two hydroxy groups, and having number average molecular weights ranging from about 700 to about 16,000, such as, for example, from about 750 to about 5000. Non-limiting examples of the high molecular weight compounds include polyester polyols, polyether polyols, polyhydroxy polycarbonates, polyhydroxy polyacetals, polyhydroxy polyacrylates, polyhydroxy polyester amides, polyhydroxy polyalkadienes and polyhydroxy polythioethers. In various embodiments, polyester polyols, polyether polyols, and polyhydroxy polycarbonates may be chosen. Mixtures of such compounds are also within the scope of the disclosure.

The polyester diol(s) may optionally be prepared from aliphatic, cycloaliphatic, or aromatic dicarboxylic or polycarboxylic acids, or anhydrides thereof; and dihydric alcohols such as diols chosen from aliphatic, alicyclic, or aromatic diols.

The aliphatic dicarboxylic or polycarboxylic acids may be chosen from, for example: succinic, fumaric, glutaric, 2,2-dimethylglutaric, adipic, itaconic, pimelic, suberic, azelaic, sebacic, maleic, malonic, 2,2-dimethylmalonic, nonanedicarboxylic, decanedicarboxylic, dodecane¬dioic, 1,3-cyclohexanedicarboxylic, 1,4-cyclo¬hexane-dicarboxylic, 2,5-norboranedicarboxylic, diglycolic, thiodipropionic, 2,5-naphthalene-dicarboxylic, 2,6-naphthalene¬dicarboxylic, phthalic, terephthalic, isophthalic, oxanic, o-phthalic, tetrahydrophthalic, hexahydrophthalic or trimellitic acid.

The acid anhydrides may, in further exemplary embodiments, be chosen from o-phthalic, trimellitic or succinic acid anhydride or a mixture thereof. By way of non-limiting example only, the dicarboxylic acid may be adipic acid.

The dihydric alcohols may be chosen from, for example, ethanediol, ethylene glycol, diethylene glycol, triethylene glycol, trimethylene glycol, tetraethylene glycol, 1,2-propanediol, dipropylene glycol, tripropylene glycol, tetrapropylene glycol, 1,3-propanediol, 1,4-butanediol, 1,3-butanediol, 2,3-butanediol, 1,5-pentanediol, 1,6-hexanediol, 2,2-dimethyl-1,3-propanediol, 1,4-dihydroxycyclohexane, 1,4-dimethylolcyclohexane, cyclohexanedimethanol, 1,8-octanediol, 1,10-decanediol, 1,12-dodecanediol, neopentyl glycol, and mixtures thereof. The cycloaliphatic and/or aromatic dihydroxyl compounds may also be suitable as the dihydric alcohol(s) for the preparation of the polyester polyol(s).

The polyester diols may also be chosen from homopolymers or copolymers of lactones, which are, in at least certain embodiments, obtained by addition reactions of lactones or lactone mixtures, such as butyrolactone, ε-caprolactone and/or methyl-ε-caprolactone with the appropriate polyfunctional, e.g. difunctional, starter molecules such as, for example, the dihydric alcohols mentioned above. The corresponding polymers of ε-caprolactone may be chosen in at least some embodiments.

The polyester polyol, e.g. polyester diol, radical R1, may be obtained by polycondensation of dicarboxylic acids, such as adipic acid, with polyols, e.g. diols, such as hexanediol, neopentyl glycol, and mixtures thereof.

The polycarbonates containing hydroxyl groups comprise those known per se, such as the products obtained by reacting diols, such as (1,3)-propanediol, (1,4)-butanediol and/or (1,6)-hexanediol, diethylene glycol, triethylene glycol, or tetraethylene glycol with diaryl carbonates, for example diphenyl carbonate or phosgene.

Optional polyether polyols may be obtained in any known manner by reacting starting compounds which contain reactive hydrogen atoms with alkylene oxides, such as, for example, ethylene oxide; propylene oxide; butylene oxide; styrene oxide; tetrahydrofuran; or epichlorohydrin, or with mixtures of these alkylene oxides. In at least certain embodiments, the polyethers do not contain more than about 10% by weight of ethylene oxide units. For example, polyethers obtained without addition of ethylene oxide may be chosen.

Polyethers modified with vinyl polymers are also suitable according to various embodiments of the disclosure. Products of this type can be obtained by polymerization, for example, of styrene and acrylonitrile in the presence of polyethers, for example as described in U.S. Pat. Nos. 3,383,351; 3,304,273; 3,523,095; 3,110,695; and German patent 1 152 536.

Among the polythioethers which may be chosen include the condensation products obtained from thiodiglycol per se and/or with other glycols, dicarboxylic acids, formaldehyde, aminocarboxylic acids, and/or amino alcohols. The products obtained are either mixed polythioethers, polythioether esters, or polythio¬ether ester amides, depending on the co-components.

Optional polyacetals include but are not limited to the compounds which can be prepared from aldehydes, for example formaldehyde, and from glycols, such as diethylene glycol, triethylene glycol, ethoxylated 4,4'-(dihydroxy)diphenyl-dimethylmethane, and (1,6)-hexane¬diol. Polyacetals useful according to various non-limiting embodiments of the disclosure can also be prepared by polymerization of cyclic acetals.

Optional polyhydroxy polyesteram ides and polyamines include, for example, the mainly linear condensation products obtained from saturated or unsaturated, polybasic carboxylic acids or anhydrides thereof, and from saturated or unsaturated, polyvalent amino alcohols, from diamines, or from polyamines, as well as mixtures thereof.

Optional monomers for the production of polyacrylates having hydroxyl functionality comprise acrylic acid, methacrylic acid, crotonic acid, maleic anhydride, 2-hydroxyethyl acrylate, 2-hydroxyethyl methacrylate, 2-hydroxypropyl acrylate, 2-hydroxypropyl methacrylate, 3-hydroxypropyl acrylate, 3-hydroxypropyl methacrylate, glycidyl acrylate, glycidyl methacrylate, 2-isocyanatoethyl acrylate, and 2-isocyanatoethyl methacrylate.

Mixtures of dihydroxy compounds can also be chosen.

Optional polyisocyanates for providing the hydrocarbon-based radical R2 include, for example, organic diisocyanates having a molecular weight ranging from about 100 to about 1500, such as about 112 to about 1000, or about 140 to about 400.

Optional diisocyanates are those chosen from the general formula R2(NCO)2, in which R2 represents a divalent aliphatic hydrocarbon group comprising from about 4 to 18 carbon atoms, a divalent cycloaliphatic hydrocarbon group comprising from about 5 to 15 carbon atoms, a divalent araliphatic hydrocarbon group comprising from about 7 to 15 carbon atoms, or a divalent aromatic hydrocarbon group comprising from about 6 to 15 carbon atoms. Examples of the organic diisocyanates which may be chosen include, but are not limited to, tetramethylene diisocyanate, 1,6-hexamethylene diisocyanate, dodecamethylene diisocyanate, cyclohexane-1,3-diisocyanate and cyclohexane-1,4-diisocyanate, 1-isocyanato-3-isocyanato¬methyl-3,5,5-trimethylcyclohexane (isophorone diisocyanate or IPDI), bis(4-isocyanatocyclohexyl)-methane, 1,3-bis(isocyanatomethyl)cyclohexane and 1,4-bis(isocyanatomethyl)cyclohexane and bis(4-isocyanato-3-methylcyclohexyl)methane. Mixtures of diisocyanates can also be used.

In at least certain embodiments, diisocyanates are chosen from aliphatic and cycloaliphatic diisocyanates. For example, 1,6-hexamethylene diisocyanate, isophorone diisocyanate, and dicyclohexylmethane diisocyanate, as well as mixtures thereof may be chosen.

The use of diols, for example low molecular weight diols, R3, may in at least certain embodiments allow a stiffening of the polymer chain. The expression "low molecular weight diols" means diols having a molecular weight ranging from about 50 to about 800, such as about 60 to 700, or about 62 to 200. They may, in various embodiments, contain aliphatic, alicyclic, or aromatic groups. In certain exemplary embodiments, the compounds contain only aliphatic groups. The diols that may be chosen may optionally have up to about 20 carbon atoms, and may be chosen, for example, from ethylene glycol, diethylene glycol, propane-1,2-diol, propane-1,3-diol, butane-1,4-diol, 1,3-butylene glycol, neopentyl glycol, butylethylpropanediol, cyclohexanediol, 1,4-cyclohexanedimethanol, hexane-1,6-diol, bisphenol A (2,2-bis(4-hydroxyphenyl)propane), hydrogenated bisphenol A (2,2-bis(4-hydroxy¬cyclo¬hexyl)-propane), and mixtures thereof. For example, R3 may be derived from neopentyl glycol.

Optionally, the low molecular weight diols may contain ionic or potentially ionic groups. Suitable low molecular weight diols containing ionic or potentially ionic groups may be chosen from those disclosed in U.S. Pat. No. 3,412,054. In various embodiments, compounds may be chosen from dimethylohbutanoic acid (DMBA), dimethylolpropionic acid (DMPA), and carboxyl-containing caprolactone polyester diol. If low molecular weight diols containing ionic or potentially ionic groups are chosen, they may, for example, be used in an amount such that less than about 0.30 meq of —COOH is present per gram of polyurethane in the polyurethane dispersion. In at least certain exemplary and non-limiting embodiments, the low molecular weight diols containing ionic or potentially ionic groups are not used.

Reaction product (ii) may be chosen from at least one chain extender according to the formula:

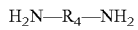

wherein $R_4$ is chosen from alkylene or alkylene oxide radicals, said radicals not being substituted with ionic or potentially ionic groups.

Reaction product (ii) may optionally be chosen from alkylene diamines, such as hydrazine, ethylen¬diamine, propylenediamine, 1,4-butylenediamine and piperazine; and alkylene oxide diamines such as dipropylamine diethylene glycol (DPA-DEG available from Tomah Products, Milton, WI), 2-methyl-1,5-pentanediamine (Dytec A from DuPont), hexanediamine, isophorone¬diamine, and 4,4-methylenedi (cyclohexylamine), and the DPA-series of ether amines available from Tomah Products, Milton, WI, including dipropylamine propylene glycol, dipropylamine dipropylene glycol, dipropylamine tripropylene glycol, dipropylamine poly(propylene glycol), dipropylamine ethylene glycol, dipropylamine poly(ethylene glycol), dipropylamine 1,3-propanediol, dipropylamine 2-methyl-1,3-propanediol, dipropylamine 1,4-butanediol, dipropylamine 1,3-butanediol, dipropylamine 1,6-hexanediol and dipropylamine cyclohexane-1,4-dimethanol, and mixtures thereof.

Reaction product (iii) may be chosen from at least one chain extender according to the formula:

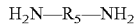

wherein $R_5$ is chosen from alkylene radicals substituted with ionic or potentially ionic groups. In at least certain exemplary embodiments, the compounds may have an ionic or potentially ionic group and two isocyanate-reactive groups.

As used herein, ionic or potentially ionic groups may include groups comprising ternary or quaternary ammonium groups, groups convertible into such groups, carboxyl groups, carboxylate groups, sulphonic acid groups, and sulphonate groups. At least partial conversion of the groups convertible into salt groups of the type mentioned may take place before or during the mixing with water. Specific compounds include diaminosulphonates, such as for example the sodium salt of N-(2-aminoethyl)-2-aminoethanesulphonic acid (AAS) or the sodium salt of N-(2-aminoethyl)-2-aminopropionic acid.

In at least certain embodiments, R5 represents an alkylene radical substituted with sulphonic acid or sulphonate groups. By way of example only, the compound is chosen from sodium salts of N-(2-aminoethyl)-2-aminoethanesulphonic acid.

By way of non-limiting example, such polyurethane latex polymers include, but are not limited to, aqueous polyurethane dispersions comprising a reaction product of a prepolymer such as, for example, those sold under the BAYCUSAN® name by Bayer such as, for example, BAYCUSAN® C1000 (INCI name: Polyurethane-34), BAYCUSAN® C1001 (INCI name: Polyurethane-34), BAYCUSAN® C1003 (INCI name: Polyurethane-32), BAYCUSAN® C1004 (INCI name: Polyurethane-35) and BAYCUSAN® C1008 (INCI name: Polyurethane-48). In various exemplary embodiments, polyurethane latexes may be chosen from, but are not limited to, aqueous polyurethane dispersion of Isophthalic Acid/Adipic Acid/Hexylene Glycol/Neopentyl glycol/Dimethylolpropanoic Acid/Isophorone Diisocyanate copolymer (INCI name: Polyurethane-1, such as LUVISET® P.U.R, BASF), polycarbonate polyurethane, aliphatic polyurethane and aliphatic polyester polyurethane (such as the NEOREZ® series, DSM, such as NEOREZ® R989, and NEOREZ® R-2202).

Bis-Urea Derivatives

Bis-urea derivatives useful in the instant hair-treatment compositions include those of the following formula:

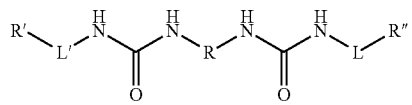

wherein R is a $C_3$-$C_{18}$ linear, branched, or cyclic moiety; and R' and R" may be the same or different and are selected from the group consisting of $C_1$-$C_{36}$ linear or branched alkanes or aryl alkanes, α-methyl branched $C_2$-$C_{36}$ alkanes, α-methyl branched $C_2$-$C_{36}$ ethers, β-methyl branched $C_2$-$C_{36}$ alkanes, and β-methyl branched $C_2$-$C_{36}$ ethers, wherein if R' and R" and the same, then both of said groups is selected from the group consisting of α-methyl branched $C_2$-$C_{18}$ ethers and β-methyl branched $C_2$-$C_{18}$ ethers; wherein L and L' may be same or different and are selected from the group consisting of ethylene oxide chains, propylene oxide chains, and mixtures thereof.

In some instances, the bis-urea derivatives may include those of the following formula:

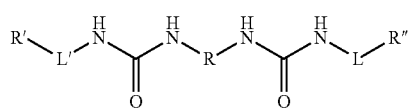

wherein R is a $C_3$-$C_{18}$ linear or branched alkylene chain or an aromatic ring; and R' and R" may be the same or different and are selected from the group consisting of $C_1$-$C_{36}$ linear or branched alkanes or aryl alkanes, α-methyl branched $C_2$-$C_{36}$ alkanes, α-methyl branched $C_2$-$C_{36}$ ethers, β-methyl branched $C_2$-$C_{36}$ alkanes, and β-methyl branched $C_2$-$C_{36}$ ethers; wherein if R' and R" and the same, then both of said groups is selected from the group consisting of α-methyl branched $C_2$-$C_{18}$ ethers and β-methyl branched $C_2$-$C_{18}$ ethers; wherein L and L' may be same or different and are selected from the group consisting of ethylene oxide chains, propylene oxide chains, and mixtures thereof, and the chains may comprise one or a plurality of repeat units.

In some instances, the bis-urea derivatives may include those of the following formula:

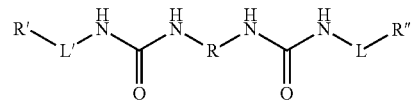

wherein R is a $C_3$-$C_{18}$ linear, branched or cyclic moiety selected from the group consisting of unsubstituted or substituted phenyl, phenyl ether, and phenyl methylene; and R' and R" may be the same or different and are selected from the group consisting of $C_1$-$C_{36}$ linear or branched alkanes, α-methyl branched $C_2$-$C_{36}$ alkanes or aryl alkanes, α-methyl branched $C_2$-$C_{36}$ ethers, β-methyl branched $C_2$-$C_{36}$ alkanes, and β-methyl branched $C_2$-$C_{36}$ ethers; wherein if R' and R" and the same, then both of said groups is selected from the group consisting of α-methyl branched $C_2$-$C_{18}$ ethers and β-methyl branched $C_2$-$C_{18}$ ethers; wherein L and L' may be same or different and are selected from the group consisting of ethylene oxide chains, propylene oxide chains, and mixtures thereof, and the chains may comprise one or a plurality of repeat units.

In particular, the bis-urea derivative may be a compound of the following formula:

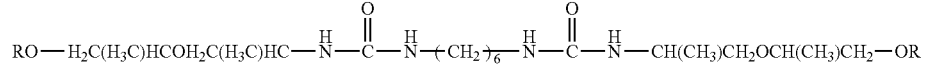

wherein R is a $C_1$-$C_{36}$ linear or branched alkane, a $C_6$-$C_{24}$ linear or branched alkane, or a $C_{10}$-$C_{16}$ linear or branched alkane. A non-limiting example of a bis-urea derivative, such as those described above is as follows:

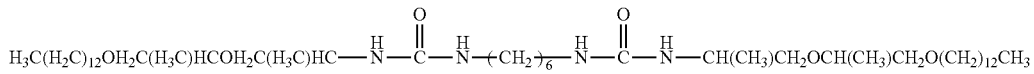

Bis-urea derivatives (such as those described above) and methods for manufacturing the bis-urea derivatives are described in U.S. Pat. No. 8,668,918, which is incorporated herein by reference in its entirety. INCI: Bis-(C12-14 alkyl PPG-4) Hexamethylenediurea is commercially available as Millithix® MT-800 (Milliken).

Solvents

The solvents are typically hydrophobic and/or non-polar. Examples of suitable solvents include, but are not limited to, oils, mineral white oils, solvents, base oils, technical mineral oils, synthetic hydrocarbons, solid hydrocarbons, semi-solid hydrocarbons, waxes, petroleum distillates, petrolatums, and a mixture thereof. In some instances, the solvent may be paraffinic or naphthenic oil.

Further, non-limiting examples include a diglyceride, a PPG alkyl ether, a therapeutic oil, acetylated lanolin alcohol, alexandria laurel tree oil, alkyl benzoate, alkyl octanoate, almond oil, an essential oil, an unsaturated or polyunsaturated oil, apricot stone oil, arachidyl behenate, arachidyl propionate, avocado oil, barley oil, basil oil, beeswax, benzyl laurate, benzyl myristate, benzyl palm itate, bis(octyldodecyl stearoyl) dimer dilinoleate, borage seed oil, butyl myristate, butyl stearate, C12-C15 alkyl benzoate, C12-C15 alkyl octanoate, calendula oil, camphor oil, canelle nut tree oil, canola oil, capric/caprylic triglycerides, caprylic/capric triglyceride castor oil, cardamom oil, carrot oil, castor oil, cetearyl ethylhexanoate, cetearyl isononanoate, cetearyl octanoate, cetyl acetate, cetyl ethylhexanoate, cetyl lactate, cetyl myristate, cetyl octanoate, cetyl palmitate, cetyl ricinoleate, citronella oil, clary sage oil, clove oil, cocoglycerides, coconut oil, cod-liver oil, corn oil, cotton oil, cottonseed oil, cypress oil, decyl oleate, diethyleneglycol diethylhexanoate, diethyleneglycol diisononanoate, diethyleneglycol dioctanoate, diethylhexanoate, diethylhexyl adipate, diethylhexyl malate, diethylhexyl succinate, diisopropyl adipate, diisopropyl dimerate, diisopropyl sebacate, diisosteary dimer dilinoleate, diisostearyl fumerate, dioctyl malate, dioctyl sebacate, disopropyl adipate, dodecyl oleate, essential oils, ester derivatives of lanolic acid, ester oils, ethylhexyl cocoate, ethylhexyl ethylhexanoate, ethylhexyl hydroxystarate, ethylhexyl isononanoate, ethylhexyl palm itate, ethylhexyl palmytate, ethylhexyl pelargonate, ethylhexyl stearate, evening primrose oil, flaxseed oil, frankincense oil, gelled mineral oil, ginger oil, glycereth triacetate, glycerol triheptanoate, glyceryl oleate, glyceryl trioctanoate, glyceryl triundecanoate, grape seed oil, grapefruit oil, groundnut oil, hard fat, hazelnut oil, heavy mineral oil, hempseed oil, herring oil, hexadecyl stearate, hexyl laurate, hydrocarbon oils, hydrogenated castor oil, hyssop oil, isoamyl laurate, isocetearyl octanoate, isocetyl isocetyl behenate, isocetyl lanolate, isocetyl palm itate, isocetyl salicylate, isocetyl stearate, isocetyl stearoyl stearate, isodecyl ethylhexanoate, isodecyl isononanoate, isodecyl oleate, isododecane, isohexadecane isododecane, isohexadecanol, isohexyl decanoate, isononyl isononanoate, isononyl octanoate, isoparaffin, isopropyl isostearate, isopropyl lanolate, isopropyl laurate, isopropyl myristate, isopropyl palm itate, isopropyl stearate, isosteary citrate, isosteary salicylate, isosteary tartarate, isostearyl behenate, isostearyl erucate, isostearyl glycolate, isostearyl isononanoate, isostearyl isostearate, isostearyl lactate, isostearyl linoleate, isostearyl linolenate, isostearyl malate, isostearyl neopentanoate, isostearyl palmitate, isotridecyl isononanoate, jasmine oil, jojoba oil, lauryl lactate, lavender oil, lemon oil, light mineral oil, liquid paraffin, liquid triglycerides, lucerne oil, maize germ oil, maleated soybean oil, mandarin oil, manuka oil, marjoram oil, marrow oil, MCT oil, millet oil, mineral oil, myristyl lactate, myristyl myristate, myristyl neopentanoate, myristyl propionate, myrrh oil, neopentylglycol dicaprate, neopentylglycol dicaprylate/dicaprate, neroli oil, nutmeg oil, octyl palmitate, octyl stearate, octyldodecanol, octyldodecyl behenate, octyldodecyl hydroxystearate, octyldodecyl myristate, octyldodecyl stearoyl stearate, oils from animal origin, oils of plant origin, oleyl erucate, oleyl lactate, oleyl oleate, olive oil, palm oil, passionflower oil, peanut oil, pentaerythrityl tetrastearate, petitgrain oil, petrolatum, polyisobutylene, polyolefin, poppy oil, PPG alkyl ethers, PPG-10 cetyl ether, PPG-10 oleyl ether, PPG-11 stearyl ether, PPG-12 butyl ether, PPG-14 butyl ether, PPG-15 butyl ether, PPG-15 stearyl ether, PPG-16 butyl ether, PPG-17 butyl ether, PPG-18 butyl ether, PPG-2 butyl ether, PPG-2 methyl ether, PPG-20 butyl ether, PPG-20 oleyl ether, PPG-22 butyl ether, PPG-23 oleyl ether, PPG-24 butyl ether, PPG-26 butyl ether, PPG-28 cetyl ether, PPG-3 methyl ether, PPG-3 myristyl ether, PPG-30 butyl ether, PPG-30 cetyl ether, PPG-30 isocetyl ether, PPG-30 oleyl ether, PPG-33 butyl ether, PPG-37 oleyl ether, PPG-4 butyl ether, PPG-4 lauryl ether, PPG-4 myristyl ether, PPG-40 butyl ether, PPG-5 butyl ether, PPG-50 cetyl ether, PPG-50 oleyl ether, PPG-52 butyl ether, PPG-53 butyl ether, PPG-7 lauryl ether, PPG-9 butyl ether, PPG-9-13 butyl ether, propyl myristate, propylene glycol dicaprate, propylene glycol dicaprylate, propylene glycol myristyl ether acetate, propylene glycol ricinoleate, rapeseed oil, rosehip oil, rye oil, safflower oil, sage oil, salmon oil, sesame oil, shea butter, soya oil, soybean oil, stearyl caprate, stearyl heptanoate, stearyl propionate, sunflower oil, sweet almond oil, synthetic isoalkane, sysymbrium oil, syzigium aromaticum oil, tangerine oil, tea tree oil, therapeutic oils, tocopheryl acetate, tocopheryl linoleate, tridecyl ethylhexanoate, tridecyl isononanoate, triisocetyl citrate, unsaturated or polyunsaturated oils, vanilla oil, verbena oil, walnut oil, wheat germ glycerides, wheat germ oil, white petrolatum and mixtures thereof.

Examples of suitable commercially available hydrophobic, non-polar solvents include, but are not limited to EXCEL 260-HC which is available from Excel Paralubes; ISOPAR L, ISOPAR M, and ISOPAR V which are available from Exxon Chemical; DRAKEOL 7, DRAKEOL 31, DRAKEOL 34, Snow White Petrolatum, and Amber Petrolatum which are available from Penreco; CONOSOL C145, CONOSOL 200, CONOSOL 260, and CONOSOL V 340 which are available from Conoco, Inc.; PERMETHYL 99A, PERMETHYL 101A, and PERMETHYL 102A which are available from Presperse; and PANALANE L14E which is available from Amoco.

In some instances, the solvent may be selected from the group consisting of oils, mineral oil, fatty alcohols, fatty acids, fatty alcohol derivatives, fatty acid derivatives (such as alkoxylated fatty acids or polyethylene glycol esters of fatty acids or propylene glycol esters of fatty acids or butylene glycol esters of fatty acids or esters of neopentyl glycol and fatty acids or polyglycerol/glycerol esters of fatty acids or glycol diesters or diesters of ethylene glycol and fatty acids or esters of fatty acids and fatty alcohols, esters of short chain alcohols and fatty acids), esters of fatty alcohols, hydroxy-substituted fatty acids, waxes, triglyceride compounds, lanolin, and a mixture thereof. For instance, one or more fatty compounds may be selected from the group consisting of glycol distearate, PEG-55 propylene glycol oleate, cetearyl alcohol, soybean oil, cetyl esters, isopropyl myristate, cetearyl alcohol, orbigynya oleifera seed oil, propylene glycol dicaprylate/dicaprate, mineral oil, and a mixture thereof.

Non-limiting examples of the fatty alcohols, fatty acids, fatty alcohol derivatives, and fatty acid derivatives are found in International Cosmetic Ingredient Dictionary, Sixteenth Edition, 2016, which is incorporated by reference herein in its entirety.

Fatty alcohols useful herein include those having from about 10 to about 30 carbon atoms, from about 12 to about 22 carbon atoms, and from about 16 to about 22 carbon atoms. These fatty alcohols can be straight or branched chain alcohols and can be saturated or unsaturated. Nonlimiting examples of fatty alcohols include decyl alcohol, undecyl alcohol, dodecyl, myristyl, cetyl alcohol, stearyl alcohol, isostearyl alcohol, isocetyl alcohol, behenyl alcohol, linalool, oleyl alcohol, cholesterol, cis4-t-butylcyclohexanol, myricyl alcohol and a mixture thereof. In some cases, the fatty alcohols are those selected from the group consisting of cetyl alcohol, stearyl alcohol, isostearyl alcohol, oleyl alcohol, and a mixture thereof.

Fatty acids useful herein include those having from about 10 to about 30 carbon atoms, from about 12 to about 22 carbon atoms, and from about 16 to about 22 carbon atoms. These fatty acids can be straight or branched chain acids and can be saturated or unsaturated. Also included are diacids, triacids, and other multiple acids which meet the carbon number requirement herein. Also included herein are salts of these fatty acids. Nonlimiting examples of fatty acids include lauric acid, palm itic acid, stearic acid, behenic acid, arichidonic acid, oleic acid, isostearic acid, sebacic acid, and a mixture thereof. In some cases, the fatty acids are selected from the group consisting of palm itic acid, stearic acid, and a mixture thereof.

Fatty alcohol derivatives include alkyl ethers of fatty alcohols, alkoxylated fatty alcohols, alkyl ethers of alkoxylated fatty alcohols, esters of fatty alcohols and a mixture thereof. Nonlimiting examples of fatty alcohol derivatives include materials such as methyl stearyl ether; 2-ethylhexyl dodecyl ether; stearyl acetate; cetyl propionate; the ceteth series of compounds such as ceteth-1 through ceteth-45, which are ethylene glycol ethers of cetyl alcochol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; C1-C30 alkyl ethers of the ceteth, steareth, and ceteareth compounds just described; polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; and a mixture thereof.

Non-limiting olyglycerol esters of fatty acids include those of the following formula:

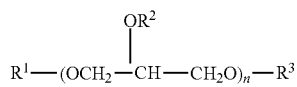

wherein the average value of n is about 3 and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$. For example, glyceryl monomyristate, glyceryl monopalmitate, glyceryl monostearate, glyceryl isostearate, glyceryl monooleate, glyceryl ester of mono(olive oil fatty acid), glyceryl dioleate and glyceryl distearate. Additionally, non-limiting examples of nonionic polyglycerol esters of fatty acids include polyglyceryl-4 caprylate/caprate, polyglyceryl-10 caprylate/caprate, polyglyceryl-4 caprate, polyglyceryl-10 caprate, polyglyceryl-4 laurate, polyglyceryl-5 laurate, polyglyceryl-6 laurate, polyglyceryl-10 laurate, polyglyceryl-10 cocoate, polyglyceryl-10 myristate, polyglyceryl-10 oleate, polyglyceryl-10 stearate, and a mixture thereof.

The fatty acid derivatives are defined herein to include fatty acid esters of the fatty alcohols as defined above, fatty acid esters of the fatty alcohol derivatives as defined above when such fatty alcohol derivatives have an esterifiable hydroxyl group, fatty acid esters of alcohols other than the fatty alcohols and the fatty alcohol derivatives described above, hydroxy-substituted fatty acids, and a mixture thereof. Nonlimiting examples of fatty acid derivatives inlcude ricinoleic acid, glycerol monostearate, 12-hydroxy stearic acid, ethyl stearate, cetyl stearate, cetyl palm itate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, and a mixture thereof. Preferred for use herein are glycerol monostearate, 12-hydroxy stearic acid, and a mixture thereof.

In some cases, the solvent may be one or more high melting point fatty compounds. A high melting point fatty compound is a fatty compound having a melting point of 25° C. Even higher metling point fatty compounds may also be used, for example, fatty compounds having a metling point of 40° C. or higher, 45° C. or higher, 50° C. or higher. The high melting point fatty compound may be selected from the group consisting of fatty alcohols, fatty acids, fatty alcohol derivatives, fatty acid derivatives, and mixtures thereof. Nonlimiting examples of the high melting point compounds are found in International Cosmetic Ingredient Dictionary, Fifteenth Edition, 2014, which is incorporated herein by reference in its entirety. The fatty alcohols useful herein are those having from about 14 to about 30 carbon atoms, preferably from about 16 to about 22 carbon atoms. These fatty alcohols are saturated and can be straight or branched chain alcohols. Non-limiting examples of high melting point fatty compounds include fatty alcohols such as, for example, cetyl alcohol (having a melting point of about 56° C.), stearyl alcohol (having a melting point of about 58-59° C.), behenyl alcohol (having a melting point of about 71° C.), and mixtures thereof. These compounds are known to have the above melting point. However, they often have lower melting points when supplied, since such supplied products are often mixtures of fatty alcohols having alkyl chain length distribution in which the main alkyl chain is cetyl, stearyl or behenyl group. In the present application, more preferred fatty alcohols are cetyl alcohol, stearyl alcohol and mixtures thereof.

Silicones

Exemplary silicones include, without limitation, cyclic silicones, such as those having 3 to 6, or 3 to 4 or 3 to 5, (or any of 3, 4, 5, or 6) Si—O groups in the cyclic backbone chain (e.g., siloxanes). In some cases, the cyclic silicone is a volatile silicone. In some cases, the cyclic silicone is a low viscosity silicone. Exemplary cyclic silicones include, without limitation, cyclomethicone, cyclotetrasiloxane, cyclopentasiloxane (e.g., Cyclomethicone 5-NF), cyclohexasiloxane and a mixture of cyclohexasiloxane and cyclopenasiloxane (e.g., DOW CORNING 246 Fluid (d6+ d5)). Other non-limiting examples of silicones are silicones having side groups or side chains. In some cases, the side groups are hydrophobic. In some cases, the side groups are straight chained, while in other embodiments the side groups are branched. Exemplary side chains include those having 1 to 6, or 2 to 6, or 3 to 6 or 3 to 6 or 5 to 6 carbons or heteroatoms (e.g., O, S, or N) (or a mixture thereof). Exemplary linear side chains include, without limitation, methyl, ethyl, propyl, butyl, pentyl, and hexyl. Exemplary branched side chains include, without limitation, isopropyl, isobutyl, and tert-butyl. In one nonlimiting embodiment, the branched side chain is —O—Si(CH$_3$)$_3$. Nonlimiting examples of silicones having branched side chains are stearyl dimethicone and phyenyltrimethicone, cetyl dimethicone, caprylyl methicone, PEG/PPG 18/18 dimethicone the structures of which are as follows:

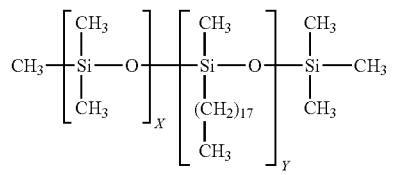

Stearyl Dimethicone

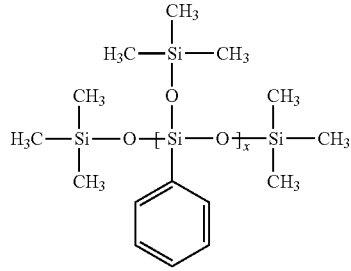

Phenyltrimethicone

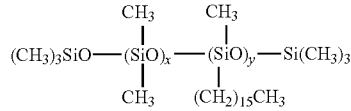

Cetyl Dimethicone

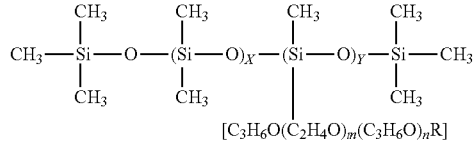

PEG/PPG 18/18 dimethicone

In the above formulas m, n, x, and y may independently be integers of 1 to 100, 1 to 80, 1 to 60, 1 to 50, 1 to 40, 1 to 30, 1 to 20, or 1 to 10. In some cases, the side chains are cyclic. Cyclic side chains include aliphatic side chains and aromatic side chains. A nonlimiting example of a cyclic side chain is phenyl.

With regard to silicones having hydrophilic or polar groups, as described previously, silicones that are repulsive with regard to the hydrophobic chains of the oil are thought to produce more stable foams because they do not inhibit the hydrophobic-hydrophobic interactions of the oil. Exemplary hydrophilic or polar groups include oxygen-containing groups, such as carbonyl groups, hydroxy groups, ether, ester, carboxylic groups, which replace one or more methyl groups. The hydrophilic/polar groups are present alternatively in the main chain of the silicone or in a side chain. Nonlimiting examples of a silicone having a hydrophilic group are PEG/PPG 18/18 dimethicone and dimethiconol, the structures of which are:

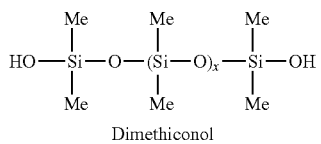

Dimethiconol

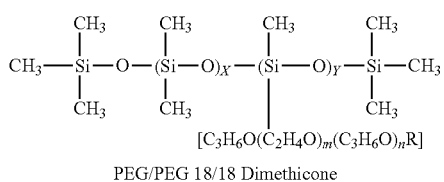

PEG/PEG 18/18 Dimethicone

X, y, m, and n are as defined above, and R is a C$_1$ to C$_{10}$ alkyl.

Another type of specific non limiting volatile silicone is a volatile short chain linear alkylmethylsilicone fluid. The volatile short chain linear alkylmethylsilicone fluid has the formula:

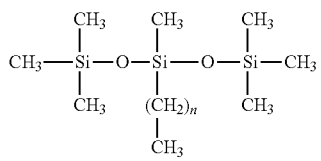

In the above formula, the integer represented by n has a value of five to twelve. Preferably, n has a value of five to eight. Compounds include, for example, 3-hexyl-1,1,1,3,5,5,5,-heptamethyltrisiloxane and 3-octyl-1,1,1,3,5,5,5-heptamethyltrisiloxane.

Yet another type of volatile silicone in accordance with the present invention is a volatile short chain linear phenylmethylsilicone fluid. The volatile short chain linear phenylmethylsilicone fluid has the formula:

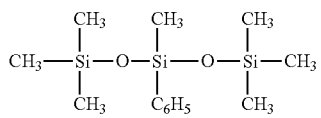

This compound is 3-phenyl-1,1,1,3,4,4,4-heptamethyltrisiloxane. Further volatile silicone fluids useful in the compositions described herein include, without limitation, are decamethylcyclopentasiloxane (DMCPS) which has a molecular weight of about 370, a refractive index of 1.40, and the formula [(Me$_2$)SiO]$_5$; the compound 3-hexyl-1,1,1,3,5,5,5-heptamethyltrisiloxane (HHMTS) which has a molecular weight of about 306, and a refractive index of 1.41; and the compound 3-phenyl-1,1,1,3,5,5,5-heptamethyltrisiloxane (PHMTS) which has a molecular weight of about 298 and a refractive index of 1.45.

As amino silicone that may be used in the scope of the instant disclosure, the following can be cited:

a) polysiloxanes corresponding to formula (A):

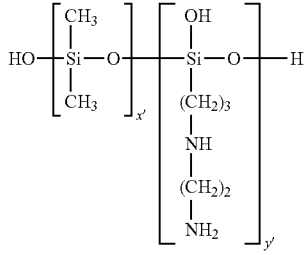

in which x' and y' are integers such that the weight-average molecular weight (Mw) is comprised between about 5000 and 500 000 b) amino silicones corresponding to formula (B):

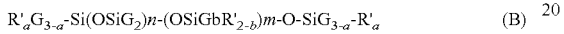

in which:
- G, which may be identical or different, designate a hydrogen atom, or a phenyl, OH or $C_1$-$C_8$ alkyl group, for example methyl, or $C_1$-$C_8$ alkoxy, for example methoxy,
- a, which may be identical or different, denote the number 0 or an integer from 1 to 3, in particular 0;
- b denotes 0 or 1, and in particular 1;
- m and n are numbers such that the sum (n+m) ranges from 1 to 2000 and in particular from 50 to 150, it being possible for n to denote a number from 0 to 1999 and in particular from 49 to 149, and form to denote a number from 1 to 2000 and in particular from 1 to 10;
- R', which may be identical or different, denote a monovalent radical having formula —$CqH_2qL$ in which q is a number ranging from 2 to 8 and L is an optionally quaternized amino group chosen from the following groups:

—NR"-Q-N(R")$_2$

—N(R")$_2$

—N+(R")$_3$A–

—N+H(R")$_2$A–

—N+H$_2$(R")A–

—N(R")-Q-N+R"H$_2$A–

—NR"-Q-N+(R")$_2$H A–

—NR"-Q-N+(R")$_3$A– in which R", which may be identical or different, denote hydrogen, phenyl, benzyl, or a saturated monovalent hydrocarbon-based radical, for example a $C_1$-$C_{20}$ alkyl radical; Q denotes a linear or branched $CrH_{2r}$ group, r being an integer ranging from 2 to 6, preferably from 2 to 4; and A-represents a cosmetically acceptable ion, in particular a halide such as fluoride, chloride, bromide or iodide.

A group of amino silicones corresponding to this definition (B) is represented by the silicones called "trimethylsilylamodimethicone" having formula (C):

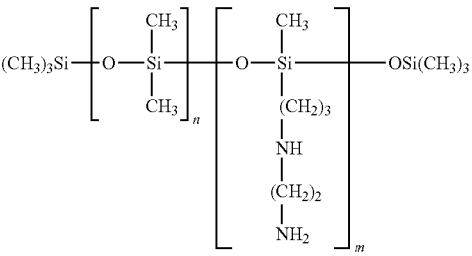

in which n and m have the meanings given above, in formula B.

Another group of amino silicones corresponding to this definition is represented by silicones having the following formulae (D) or (E):

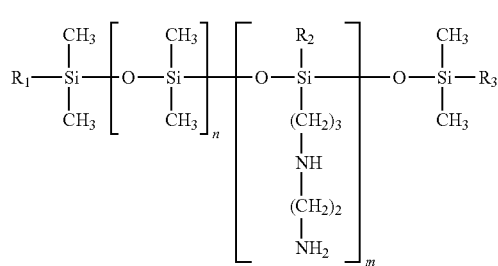

in which:
- m and n are numbers such that the sum (n+m) can range from 1 to 1000, in particular from 50 to 250 and more particularly from 100 to 200, it being possible for n to denote a number from 0 to 999 and in particular from 49 to 249, and more particularly from 125 to 175, and for m to denote a number from 1 to 1000 and in particular from 1 to 10, and more particularly from 1 to 5;
- $R_1$, $R_2$, $R_3$, which may be identical or different, represent a hydroxy or $C_1$-$C_4$ alkoxy radical, where at least one of the radicals $R_1$ to $R_3$ denotes an alkoxy radical.

The alkoxy radical is preferably a methoxy radical.

The hydroxy/alkoxy mole ratio ranges preferably from 0.2:1 to 0.4:1 and preferably from 0.25:1 to 0.35:1 and more particularly equals 0.3:1.

The weight-average molecular weight (Mw) of the silicone ranges preferably from 2000 to 1 000 000, more particularly from 3500 to 200000.

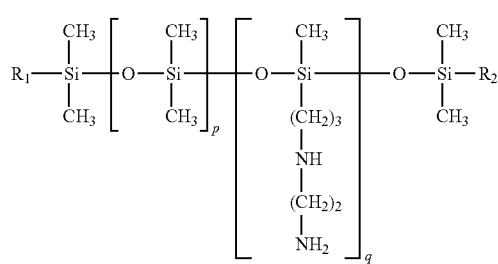

in which:
- p and q are numbers such that the sum (p+q) ranges from 1 to 1000, particularly from 50 to 350, and more particularly from 150 to 250; it being possible for p to denote a number from 0 to 999 and in particular from 49 to 349, and more particularly from 159 to 239 and for q to denote a number from 1 to 1000, in particular from 1 to 10, and more particularly from 1 to 5;
- $R_1$, $R_2$, which are different, represent a hydroxy or $C_1$-$C_4$ alkoxy radical, where at least one of the radicals $R_1$ or $R_2$ denotes an alkoxy radical.

The alkoxy radical is preferably a methoxy radical.

The hydroxy/alkoxy mole ratio ranges generally from 1:0.8 to 1:1.1 and preferably from 1:0.9 to 1:1 and more particularly equals 1:0.95.

The weight-average molecular weight (Mw) of the silicone ranges preferably from 2000 to 200000, even more particularly 5000 to 100000 and more particularly from 10 000 to 50 000.

Commercial products corresponding to these silicones having structure (D) or (E) may include in their composition one or more other amino silicones whose structure is different than formulae (D) or (E).

A product containing amino silicones having structure (D) is sold by Wacker under the name Belsil® ADM 652.

A product containing amino silicones having structure (E) is sold by Wacker under the name Fluid WR 1300®.

When these amino silicones are used, one particularly advantageous embodiment consists in using them in the form of an oil-in-water emulsion. The oil-in-water emulsion may comprise one or more surfactants. The surfactants may be of any nature but are preferably cationic and/or nonionic. The number-average size of the silicone particles in the emulsion generally ranges from 3 nm to 500 nanometres. Preferably, in particular as amino silicones having formula (E), microemulsions are used whose average particle size ranges from 5 nm to 60 nanometres (limits included) and more preferably from 10 nm to 50 nanometres (limits included). Accordingly, according to the invention the microemulsions of amino silicone having formula (E) sold as Finish CT 96 E® or SLM 28020® by Wacker can be used.

Another group of amino silicones corresponding to this definition is represented by the following formula (F):

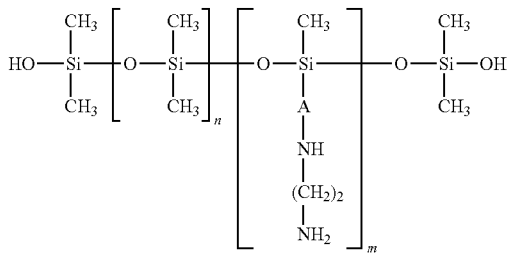

(F)

in which:
- m and n are numbers such that the sum (n+m) ranges from 1 to 2000 and in particular from 50 to 150, it being possible for n to denote a number from 0 to 1999 and in particular from 49 to 149, and form to denote a number from 1 to 2000 and in particular from 1 to 10;
- A denotes a linear or branched alkylene radical containing from 4 to 8 carbon atoms and preferably 4 carbon atoms. This radical is preferably linear.

The weight-average molecular weight (Mw) of these amino silicones ranges preferably from 2000 to 1000000 and even more particularly from 3500 to 200000.

A preferred silicone of formula (F) is amodimethicone (INCI name) sold under the tradename XIAMETER® MEM-8299 Cationic Emulsion by Dow Corning.

Another group of amino silicones corresponding to this definition is represented by the following formula (G):

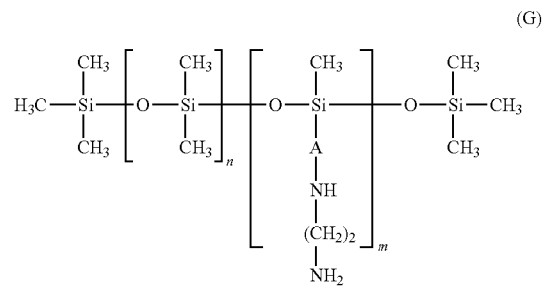

(G)

in which:
- m and n are numbers such that the sum (n+m) ranges from 1 to 2000 and in particular from 50 to 150, it being possible for n to denote a number from 0 to 1999 and in particular from 49 to 149, and form to denote a number from 1 to 2000 and in particular from 1 to 10;
- A denotes a linear or branched alkylene radical containing from 4 to 8 carbon atoms and preferably 4 carbon atoms. This radical is preferably branched.

The weight-average molecular weight (Mw) of these amino silicones ranges preferably from 500 to 1000000 and even more particularly from 1000 to 200000.

A silicone having this formula is for example DC2-8566 Amino Fluid by Dow Corning.

c) amino silicones corresponding to formula (H):

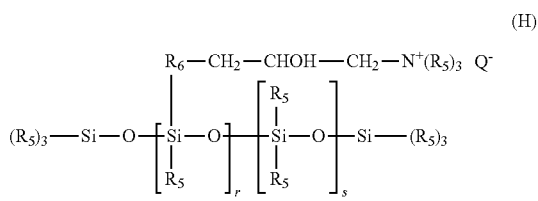

(H)

in which:
- $R_5$ represents a monovalent hydrocarbon-based radical containing from 1 to 18 carbon atoms, and in particular a $C_1$-$C_{18}$ alkyl or $C_2$-$C_{18}$ alkenyl radical, for example methyl;
- $R_6$ represents a divalent hydrocarbon-based radical, in particular a $C_1$-$C_{18}$ alkylene radical or a divalent $C_1$-$C_{18}$, for example $C_1$-$C_8$, alkylenoxy radical linked to the Si via an SiC bond;
- Q– is an anion such as a halide ion, in particular chloride, or an organic acid salt (for example acetate);
- r represents a mean statistical value from 2 to 20 and in particular from 2 to 8;
- s represents a mean statistical value from 20 to 200 and in particular from 20 to 50.

Such amino silicones are described more particularly in patent U.S. Pat. No. 4,185,087.

d) quaternary ammonium silicones having formula (I):

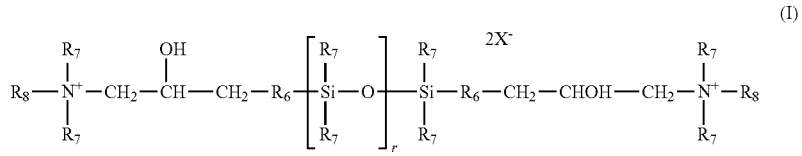

in which:
- $R_7$, which may be identical or different, represent a monovalent hydrocarbon-based radical containing from 1 to 18 carbon atoms, and in particular a $C_1$-$C_{18}$ alkyl radical, a $C_2$-$C_{18}$ alkenyl radical or a ring containing 5 or 6 carbon atoms, for example methyl;
- $R_6$ represents a divalent hydrocarbon-based radical, in particular a $C_1$-$C_{18}$ alkylene radical or a divalent $C_1$-$C_{18}$, for example $C_1$-$C_8$, alkylenoxy radical linked to the Si via an SiC bond;
- $R_8$, which may be identical or different, represent a hydrogen atom, a monovalent hydrocarbon-based radical containing from 1 to 18 carbon atoms, and in particular a $C_1$-$C_{18}$ alkyl radical, a $C_2$-$C_{18}$ alkenyl radical or a —$R_6$—$NHCOR_7$ radical;
- X– is an anion such as a halide ion, in particular chloride, or an organic acid salt (for example acetate);
- r represents a mean statistical value from 2 to 200 and in particular from 5 to 100;

These silicones are described, for example, in patent application EP-A 0 530 974.

e) amino silicones having formula (J):

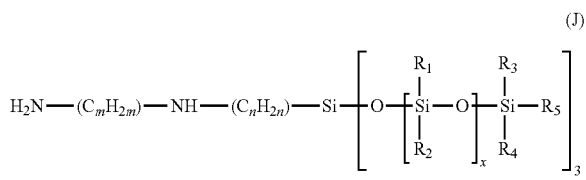

in which:
- $R_1$, $R_2$, $R_3$ and $R_4$, which may be identical or different, denote a $C_1$-$C_4$ alkyl radical or a phenyl group;
- $R_5$ denotes a $C_1$-$C_4$ alkyl radical or a hydroxyl group;
- n is an integer ranging from 1 to 5;
- m is an integer ranging from 1 to 5;
- and in which x is chosen such that the amine number is between 0.01 and 1 meq/g;

f) multiblockpolyoxyalkylenated amino silicones, of type (AB)n, A being a polysiloxane block and B being a polyoxyalkylenated block containing at least one amine group.

Said silicones are preferably constituted of repeating units having the following general formulae:

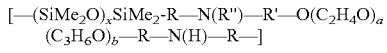

or alternatively

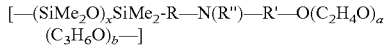

in which:
- a is an integer greater than or equal to 1, preferably ranging from 5 to 200, more particularly ranging from 10 to 100;
- b is an integer comprised between 0 and 200, preferably ranging from 4 to 100, more particularly between from 5 and 30;
- x is an integer ranging from 1 to 10 000, more particularly from 10 to 5000;
- R" is a hydrogen atom or a methyl;
- R, which may be identical or different, represent a divalent linear or branched $C_2$-$C_{12}$ hydrocarbon-based radical, optionally including one or more heteroatoms such as oxygen; preferably, R denotes an ethylene radical, a linear or branched propylene radical, a linear or branched butylene radical, or a —$CH_2CH_2CH_2OCH(OH)CH_2$— radical; preferentially R denotes a —$CH_2CH_2CH_2OCH(OH)CH_2$— radical;
- R', which may be identical or different, represent a divalent linear or branched $C_2$-$C_{12}$ hydrocarbon-based radical, optionally including one or more heteroatoms such as oxygen; preferably, R' denotes an ethylene radical, a linear or branched propylene radical, a linear or branched butylene radical, or a —$CH_2CH_2CH_2OCH(OH)CH_2$— radical; preferentially R' denotes —$CH(CH_3)$—$CH_2$—.

The siloxane blocks preferably represent between 50 and 95 mol % of the total weight of the silicone, more particularly from 70 to 85 mol %.

The amine content is preferably between 0.02 and 0.5 meq/g of copolymer in a 30% solution in dipropylene glycol, more particularly between 0.05 and 0.2.

The weight-average molecular weight (Mw) of the silicone is preferably comprised between 5000 and 1000000, more particularly between 10000 and 200000.

Mention may be made especially of the silicones sold under the names Silsoft™ A-843 or Silsoft™ A+ by Momentive.

g) the alkylamino silicones corresponding to formula (K) below:

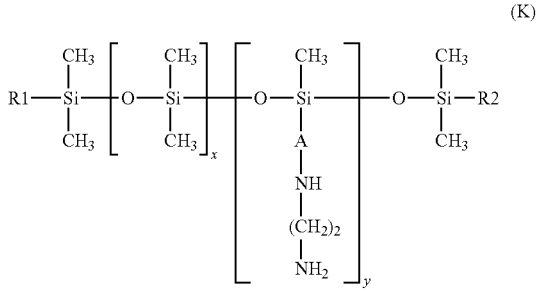

in which:
- x and y are numbers ranging from 1 to 5000; preferably, x ranges from 10 to 2000 and especially from 100 to 1000; preferably, y ranges from 1 to 100;
- $R_1$ and $R_2$, which may be identical or different, preferably identical, are linear or branched, saturated or unsaturated alkyl radicals, comprising 6 to 30 carbon atoms, preferably 8 to 24 carbon atoms and especially 12 to 20 carbon atoms;
- A denotes a linear or branched alkylene radical containing from 2 to 8 carbon atoms, Preferably, A comprises 3 to 6 carbon atoms, especially 4 carbon atoms; preferably, A is branched. Mention may be made especially of the following divalent radicals: —$CH_2CH_2CH_2$— and —$CH_2CH(CH_3)CH_2$—.

Preferably, $R_1$ and $R_2$, which may be identical or different, are saturated linear alkyl radicals comprising 6 to 30 carbon atoms, preferably 8 to 24 carbon atoms and especially 12 to 20 carbon atoms; mention may be made in particular of dodecyl, tetradecyl, pentadecyl, hexadecyl, heptadecyl, octadecyl, nonadecyl and eicosyl radicals; and preferentially, $R_1$ and $R_2$, which may be identical or different, are chosen from hexadecyl (cetyl) and octadecyl (stearyl) radicals.

Preferentially, the silicone is of formula (K) with:
- x ranging from 10 to 2000 and especially from 100 to 1000;
- y ranging from 1 to 100;
- A comprising 3 to 6 carbon atoms and especially 4 carbon atoms; preferably, A is branched; and more particularly A is chosen from the following divalent radicals: —$CH_2CH_2CH_2$— and —$CH_2CH(CH_3)CH_2$—; and
- $R_1$ and $R_2$, which may be identical or different, being linear, saturated alkyl radicals comprising 6 to 30 carbon atoms, preferably 8 to 24 carbon atoms and especially 12 to 20 carbon atoms; chosen in particular from dodecyl, tetradecyl, pentadecyl, hexadecyl, heptadecyl, octadecyl, nonadecyl and eicosyl radicals; preferentially, $R_1$ and $R_2$, which may be identical or different, being chosen from hexadecyl (cetyl) and octadecyl (stearyl) radicals.

A preferred silicone of formula (K) is bis-cetearylamodimethicone (INCI name).

Mention may be made especially of the silicone sold under the name Silsoft™ AX by Momentive.

Preferably, the amino silicones according to the invention are chosen from the amino silicones of formula (F). A preferred silicone of formula (F) is amodimethicone (INCI name) sold under the tradename XIAMETER® MEM-8299 Cationic Emulsion by Dow Corning.

Implementation of the present disclosure is provided by way of the following examples. The examples serve to illustrate the technology without being limiting in nature.

Example 1

Essentially Anhydrous Compositions

| Component | INCI US | #1 wt. % | #2 wt. % |
|---|---|---|---|
| Polyurethane | POLYURETHANE-34 | 0.2 | 0.2 |
| Bis-Urea Derivative | BIS-(C12-14 ALKYL PPG-4) HEXAMETHYLENEDIUREA | 8 | 2 |
| Solvent | C12-15 ALKYL BENZOATE | 91.3 | 97.3 |
| Water* | WATER | 0.5 | 0.5 |

*Note
that polyurethane-34 is supplied in water.

The bis-(C12-14 alkyl PPG-4) hexamethylenediurea has a gelling temperature of about 60° C. Therefore, all raw materials are added at a temperature of about 70° C. or higher so that at 65-70° C., homogenization can be stopped to allow for uniform gelling.

Example 2

Essentially Anhydrous Compositions

| Component | INCI US | #3 wt. % | #4 wt. % |
|---|---|---|---|
| Polyurethane | POLYURETHANE-34 | 1 | 0.2 |
| Bis-Urea Derivative | BIS-(C12-14 ALKYL PPG-4) HEXAMETHYLENEDIUREA | 8 | 0.5 |
| Silicone | POLYPROPYLSILSEQUIOXANE AND/OR CYCLOHEXASILOXANE | 0.9 | 25.7 |
| Solvent | C12-15 ALKYL BENZOATE, ISOPROPYL MYRISTATE, ISODODECANE, ISONONYL ISONONANOATE, AND/OR ETHYLHEXYL PALMITATE | 87.7 | 72.8 |
| Auxiliary Agent | SILICA SILICATE | 0.3 | 0.3 |
| Water* | WATER | 2.1 | 0.4 |

*Note
that polyurethane-34 is supplied in water.

Isopropyl myristate and bis-(C12-14 Alkyl PPG-4) hexamethylenediurea were combined, heated to 75-80° C., and homogenized until uniform. Separately, the silica silicate and the C12-15 alkyl benzoate were combined and then the polyurethane-34 and the polypropylsilsequioxane (and) isododecane were added. This combination was then added to the mixture of the Isopropyl myristate and bis-(C12-14 Alkyl PPG-4) and homogenized at 75-80° C. before cooling to room temperature.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

As used herein, the terms "comprising," "having," and "including" (or "comprise," "have," and "include") are used in their open, non-limiting sense.

The terms "a," "an," and "the" are understood to encompass the plural as well as the singular.

Thus, the term "a mixture thereof" is equivalent to "mixtures thereof." Throughout the disclosure, the term "a mixture thereof" may be used, following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included in a mixture). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be include, or a mixture of any two of A, B, C, D, E, F, a salt of A, a salt of B, a salt of C, a salt of D, a salt of E, and a salt of F may be included.

The expression "one or more" means "at least one" and thus includes individual components as well as mixtures/combinations.

Other than in the operating examples, or where otherwise indicated, all numbers expressing quantities of ingredients and/or reaction conditions can be modified with the "about," meaning within+/−5% of the indicated number.

Some of the various categories of components identified for the hair-treatment compositions may overlap. In such cases where overlap may exist between two or more components, a single overlapping compound does not represent more than one component. For example, a homopolymer of methyl quaternized dimethylaminoethyl methacrylate may be characterized as both a cationic polymer component and a thickening agent component. If a particular hair-treatment composition is described as including both a cationic polymer and a thickening agent, a single homopolymer of methyl quaternized dimethylaminoethyl methacrylate can serve as only the cationic polymer or only the thickening agent (the compound does not serve as both the cationic polymer and the thickening agent in the same composition).

All percentages, parts and ratios herein are based upon the total weight of the compositions of the present invention, unless otherwise indicated.

"Conditioning" as used herein means imparting to one or more hair fibers at least one property chosen from combability, moisture-retentivity, luster, shine, and softness. The state of conditioning can be evaluated by any means known in the art, such as, for example, measuring, and comparing, the ease of combability of the treated hair and of the untreated hair in terms of combing work (gm-in), and consumer perception.

The term "treat" (and its grammatical variations) as used herein refers to the application of the compositions of the present disclosure onto the surface of keratinous substrates such as hair. The term 'treat," and its grammatical variations, relates to contacting hair with the hair-treatment compositions of the present disclosure.

The term "rinse," in the context of the instant disclosure, is used as customarily understood in the hair-care/hair-treatment art. For example, when a hair-treatment composition (e.g., a shampoo, conditioner, etc.) is "rinsed" from the hair, it is understood that at least some or most of the hair-treatment composition is removed from the hair. Nonetheless, in many cases, at least a residual amount of the hair-care composition or ingredient(s) from the hair care composition remains in or on the hair. In fact, in some cases, the residual amount of remaining composition or ingredient(s) is at least in part responsible for one or more of the styling benefits imparted to the hair.

A "rinse-off" hair-treatment composition refers to a composition that is rinsed and/or washed with water either after or during the application of the composition onto the hair, and before drying and/or styling the hair. At least a portion, and typically most, of the composition is removed from the hair during the rinsing and/or washing.

The term "stable" as used herein means that the composition does not exhibit phase separation and/or crystallization for a period of time, for example, for at least 1 day (24 hours), one week, one month, or one year.

"Volatile", as used herein, means having a flash point of less than about 100° C.

"Non-volatile", as used herein, means having a flash point of greater than about 100° C.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub-ranges between, the given ranges. Thus, a range from 1-5, includes specifically 1, 2, 3, 4 and 5, as well as sub ranges such as 2-5, 3-5, 2-3, 2-4, 1-4, etc.

The term "substantially free" or "essentially free" as used herein means that there is less than about 5% by weight of a specific material added to a composition, based on the total weight of the compositions. Nonetheless, the compositions may include less than about 3 wt. %, less than about 2 wt. %, less than about 1 wt. %, less than about 0.5 wt. %, less than about 0.1 wt. %, or none of the specified material.

The term "essentially anhydrous" or "substantially anhydrous" as used herein, for example, in the context of an "essentially anhydrous hair-treatment composition" or a "substantially anhydrous hair-treatment composition" means that the composition includes less than about 5% by weight of water. Nonetheless, the composition may include less than about 4 wt. %, less than about 3 wt. %, less than about 2 wt. %, less than about 1 wt. %, less than about 0.5 wt. %, less than about 0.1 wt. % of water, less than about 0.05 wt. % water, or less than 0.01 wt. % water.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. An essentially anhydrous hair-treatment composition consisting of:
   about 0.1 to about 5 wt. % of polyurethane-34;
   about 0.5 to about 10 wt. % of BIS-(C12-14 alkyl PPG-4) hexamethylenediurea;
   about 70 to about 98 wt. % of one or more esters of fatty acids, wherein the fatty acids have from about 10 to about 30 carbon atoms;
   optionally, about 0.01 to about 40 wt. % of one or more silicones selected from the group consisting of polyorganosiloxanes, polyalkylsiloxanes, polyarylsiloxanes, polyalkarylsiloxanes, polyestersiloxanes, alkylmethylsilicone polyether copolymers, and a mixture thereof;

optionally, about 0.01 to about 5 wt. % of one or more auxiliary agents, and less than 4 wt. % of water;

wherein all percentages by weight are based on the total weight of the hair-treatment composition.

2. The essentially anhydrous hair-treatment composition of claim 1, wherein the one or more auxiliary agents is present and comprises silica silicate.

* * * * *